(12) United States Patent
McGowan

(10) Patent No.: US 7,772,146 B2
(45) Date of Patent: Aug. 10, 2010

(54) ARTIFICIAL BONE AND JOINT COMPOSITIONS

(76) Inventor: Kenneth A. McGowan, 344 Raymaley Rd., Harrison City, PA (US) 15636

( * ) Notice: Subject to any disclaimer, the term of this patent is extended or adjusted under 35 U.S.C. 154(b) by 0 days.

(21) Appl. No.: 10/924,502

(22) Filed: Aug. 24, 2004

(65) Prior Publication Data

US 2005/0049717 A1 Mar. 3, 2005

Related U.S. Application Data

(60) Provisional application No. 60/497,999, filed on Aug. 25, 2003.

(51) Int. Cl.
*C04B 35/057* (2006.01)
*C04B 35/44* (2006.01)
*A61F 2/28* (2006.01)
*A61F 2/30* (2006.01)

(52) U.S. Cl. .................. 501/123; 501/124; 501/125; 501/127; 623/16.11; 623/23.56; 623/23.57; 623/23.76; 424/422; 424/423

(58) Field of Classification Search ............. 501/123, 501/124, 125, 127, 153; 106/35; 623/16.11, 623/23.56, 23.57, 23.76; 424/422, 423
See application file for complete search history.

(56) References Cited

U.S. PATENT DOCUMENTS

| | | | | |
|---|---|---|---|---|
| 3,312,558 | A * | 4/1967 | Miller, Jr. ............... | 501/125 |
| 4,207,306 | A * | 6/1980 | Jarcho .................. | 423/633 |
| 4,218,255 | A | 8/1980 | Bajpai et al. | |
| 4,237,559 | A * | 12/1980 | Borom ................ | 623/23.51 |
| 4,652,593 | A * | 3/1987 | Kawahara et al. ........ | 523/116 |
| 4,668,295 | A * | 5/1987 | Bajpai ................. | 106/690 |
| 4,755,228 | A * | 7/1988 | Sakurai et al. .......... | 106/692 |
| 4,960,737 | A | 10/1990 | Guile et al. | |
| 5,420,087 | A * | 5/1995 | Wieland et al. .......... | 501/124 |
| 5,900,053 | A * | 5/1999 | Brothers et al. .......... | 106/678 |
| 6,206,957 | B1 * | 3/2001 | Driessens et al. ......... | 106/35 |
| 6,689,707 | B1 | 2/2004 | Beall et al. | |
| 6,713,420 | B2 | 3/2004 | Imura et al. | |
| 6,723,334 | B1 * | 4/2004 | McGee et al. ............ | 424/423 |
| 6,809,051 | B2 | 10/2004 | Beall et al. | |
| 7,025,824 | B2 * | 4/2006 | Axen et al. ............. | 106/695 |
| 7,244,301 | B2 * | 7/2007 | Axen et al. ............. | 106/35 |
| 2004/0117030 | A1 | 6/2004 | Axen et al. | |
| 2004/0126566 | A1 * | 7/2004 | Axen et al. ............. | 428/323 |
| 2004/0206273 | A1 * | 10/2004 | Hermansson et al. ...... | 106/35 |
| 2004/0237847 | A1 * | 12/2004 | Axen et al. ............. | 106/692 |
| 2006/0037514 | A1 * | 2/2006 | Hermansson et al. ...... | 106/35 |
| 2007/0224678 | A1 * | 9/2007 | McGowan et al. ........ | 435/402 |
| 2007/0233265 | A1 * | 10/2007 | McGowan .............. | 623/18.11 |

FOREIGN PATENT DOCUMENTS

| RU | 20127067 | * | 3/1999 |
|---|---|---|---|
| RU | 2156087 | * | 9/2000 |

OTHER PUBLICATIONS

Graves et al Resorbable Ceramic Implants, J. Biommed. Mat. Res. Symposium, No. 2(Part 1) pp. 91-115, 1971.*
Translation of SE 010441-1, filed Dec. 27, 2001.*
Translation PCT/SE99/01803, filed Oct. 1999.*
Definition of Ceramic, Condensed Chemical Dictionary, Hawley, Eigth edition (1974).*
Kopanda et al "Production Processes, Properties, and Applications for Calcium Aluminate Cements", Alumina Chemical Science and technology handbook, Am. ceram. Sci., pp. 171-183 (1990).*
Geiger, Greg, Bone Cement, Technology Briefs, American Ceramic Society Bulletin, Nov. 2003, p. 5, vol. 82, No. 11, American Ceramic Society.
Kalita, S.J., et al., Porous calcium aluniinate ceramics for bone-graft applications, Abstract, Journal of Materials Research, Dec. 2002, pp. 3042-3049, vol. 17, No. 12, Materials Research Society, Warrendale, Pennsylvania.
Biological Testing, A. R. Gennaro, Remington's Pharmaceutical Sciences 17th Ed.,1985, pp. 550-558.
Bioceramics: Research and Development Opportunities, Larry L. Hench, Brazilian Journal of Physics, Jun. 1992, vol. 22, No. 2, pp. 70-76.
Surface Modification of Titanium for Improvement of Interfacial Biocompatibility, Jurgen Breme et al., Metallic Biomaterial Interfaces, 2008, pp. 102-116.
Calcium Phosphate-Based Osetoinductive Materials, R. LeGeros, Chem. Rev., 2008, vol. 108, pp. 4742-4753.
NCCAM Interim Policy: Biologically Active Agents Used in Complementary and Alternative Medicine (CAM) and Placebo Materials, nih.gov/grants/guide/notice, Release Date: Apr. 29, 2005.

* cited by examiner

*Primary Examiner*—Karl E Group
(74) *Attorney, Agent, or Firm*—Craig G. Cochenour; Buchanan Ingersoll & Rooney PC

(57) ABSTRACT

The present invention provides a ceramic porous body for in-vitro and in-vivo use comprising a composition comprising a calcium aluminate (CA) containing phase and optionally at least one of an accelerator, a retarder, a surfactant, a foaming agent, a reactive alumina, water, a fiber, and a biologically active material, and combinations thereof. Ceramic compositions are provides as well as method of using the ceramic compositions and methods of manufacturing a ceramic porous body. The ceramic porous bodies of this invention may be used as artificial bones, joints, in-vitro support structures, and in-vivo support structures for cells, tissues, organs, and nerve growth and regeneration.

7 Claims, No Drawings

ARTIFICIAL BONE AND JOINT COMPOSITIONS

BENEFIT OF PRIOR PROVISIONAL PATENT APPLICATION

This utility patent application claims the benefit of co-pending U.S. Provisional Patent Application Ser. No. 60/497,999, filed Aug. 25, 2003, entitled "Artificial Bone And Joint Compositions And Methods Of Use And Manufacture" having the same named applicant as inventor, namely, Kenneth A. McGowan. The entire contents of U.S. Provisional Patent Application Ser. No. 60/497,999 is incorporated by reference into this utility patent application.

BACKGROUND OF THE INVENTION

1. Field of the Invention

The use of calcium aluminate (all associated phases, derivatives, and/or analogs thereof) as a raw material for the manufacture of artificial bone, artificial joints, in-vitro support structures, and support structure for tissue, cells, and/or organ growth and/or regeneration is provided. The use of slipcasting, slurrycasting or vibration casting in molds to generate the desired shapes of the artificial bones, joints and support structures of the invention is also provided.

2. Description of the Background Art

Current artificial joints and bones are manufactured from apatites or metal, typically titanium. They are machined to the desired shape which is a costly and production inefficient method of construction. These materials, in order to be accommodated by the host, must exhibit porosity so as to accommodate cell growth within the three dimensional structure. In particular, porosity is important where the part comes in contact with the host's natural structure (bone). This is due to the need for the host's bone to grow into and vascularize the artificial structure in order to develop the necessary bond between the two and reduce bone degeneration at the interface. Although attempts have been made in the current materials known by those skilled in the art to introduce porosity, the resulting structure is less than ideal. In most cases, artificial joints and other structures need to be replaced over time because the surrounding tissue and structure has degenerated. Pins, screws, rods and other structures are required to stabilize, bond and support the interface.

There is an identifiable need to create structures designed to support tissue growth, such as in artificial organ growth. The use of plastics as a support structure for tissue growth is known by those skilled in the art and has been accomplished by the use of organic polymers. These plastics and polymers are expensive when employed as artificial prostheses and lack porosity.

In spite of this background art, there remains a very real and substantial need for ceramic porous bodies comprising calcium aluminate, its phases, derivatives and/or analogs thereof, wherein the ceramic bodies are capable of functioning as artificial bone, artificial joints, in-vitro support structures, and in-vivo support structures for cells, tissues, organs and nerve growth and regeneration.

SUMMARY OF THE INVENTION

The present invention has met the above-described need. The porous ceramic compositions of this invention provide compositions that may be used in the manufacture of artificial porous ceramic bodies that may function as artificial bones and joints of a patient, as well as in-vitro support structures, in-vivo support structures for cells, tissues, organ and nerve growth and/or regeneration.

The present invention provides compositions comprising a calcium aluminate (CA) containing phase. Optionally, the compositions comprise at least one of a fiber, an accelerator, a retarder, a surfactant, a foaming agent, water, a biologically active material, one or more reactive aluminas, a source of phosphate, and combinations thereof. In a preferred embodiment, the compositions provide wherein the calcium aluminate containing phase results from the interaction of $C_nA_y$, $C_nA_y$-hydrates, CaO, $Al_nO_y$-hydrates with $P_nO_y^x$ to form CAX, wherein n is an integer from about 1 to about 12, y is an integer from about 1 to about 24, and x is an integer from about 1 to about 12.

The present invention also provides for a method of making an artificial porous ceramic body comprising mapping a patient's identified bone structure, creating a three dimensional pattern of said identified bone structure from said mapped bone structure, creating a mold or negative of said identified bone structure from said pattern, casting said mold employing a composition comprising a calcium aluminate containing phase (CA) to form said artificial porous body. The compositions may be any of the compositions of this invention as described herein.

The present invention provides a porous ceramic body for in vitro and in vivo use comprising the compositions of this invention as described herein. The porous ceramic body of this invention has a porosity suitable for achieving vascularity.

Further, this invention provides for a method of using the ceramic porous composition of the present invention as described herein for producing artificial structures for use in-vitro or in-vivo by a patient comprising employing a porous ceramic composition of this invention, placing the porous ceramic composition into a mold wherein said mold matches a patient's identified structure to form an artificial structure.

The compositions, porous ceramic bodies and methods of this invention will be more fully understood from the following descriptions of the invention and the claims appended hereto.

DETAILED DESCRIPTION OF THE INVENTION

Calcium aluminate (hereinafter "CA") and its representative phases, analogs, and derivatives (including such as for example the introduction of phosphate containing phases resulting from the interaction of $C_nA_y$, $C_nA_y$-Hydrates, CaO, $Al_nO_y$, and $Al_nO_y$-hydrates with $P_nO_y^x$-referred herein as "CAX") are better alternatives as an artificial material, wherein preferably, n is an integer from about 1 to 12 and y is an integer from about 1 to 24, and x is an integer from about 1 to 12. There are several reasons for this including the fact that CAX contains hydratable compounds that introduce needed strength into the matrix. Porosity is easily introduced into the structure via the aggregate itself and/or through the use of a foaming agent. The resulting ceramic matrix can be cast to a specific shape with ease using casting technology known by those persons skilled in the art, such as including, slip casting, slurry casting or vibration casting into molds to generate a desired shape. The resulting material is chemically compatible with bone and other biological processes. The resulting shape can be high fired to make it unreactive with its environment, if desired, or, it can be partially fired to leave it somewhat active. Furthermore, a hollow cavity within the structure can be created to better allow vascularity to occur and to allow marrow to exist if indeed the body will begin to produce it with the presence of vascularity. Both conditions of vascularity and marrow growth will foster the progress of each process.

The present invention provides an artificial prosthesis having the CAX material as a structure to support tissue growth. It can be pre-engineered to match the desired finished structure and in addition, in the form of hydrates, these materials will slowly be metabolized by the body. Because of the nature of the compounds, they can easily be derivatized and functionalized for use with biological processes, such as for example, but not limited to, accommodating protein building blocks, and binding sites.

The present invention provides artificial prosthesis structures and a method for the manufacture of an artificial prosthesis. The method includes mapping the structure of interest by digitizing data from MRI scans (if soft tissue), X-ray data (if bone structure) or a combination of both, digitizing the data to create a three dimensional pattern or blank of the structure as known by those skilled in the art, utilizing the blank or pattern to create a mold or negative of the structure of interest, casting within the mold CA, CAX, and/or derivatives, and/or analogs of CA or CAX, of this invention, and optionally adding biologically active materials to produce an artificial prosthesis. The resulting artificial prosthesis is then further processed, if desired. This may involve a firing process to fix certain desired mineralogical phases and/or chemically activated by an immersion process known by those persons skilled in the art.

The present invention provides a porous ceramic body for in vitro and in vivo use comprising a calcium aluminate (CA) containing phase. In preferred embodiments of this invention the porous ceramic body further comprises one of a foaming agent, a fiber, a source of phosphate, an accelerator, a retarder, a surfactant, reactive alumina, a biologically active material, and combinations thereof.

In another embodiment of this invention the porous ceramic body as described includes wherein the calcium aluminate containing phase comprises one or more phases, analogs and derivatives of calcium aluminate.

In a preferred embodiment of this invention, the porous ceramic body as described herein includes wherein the calcium aluminate containing phase results from the interaction of $C_nA_y$, $C_nA_y$-hydrates, CaO, $Al_nO_y$-hydrates with $P_nO_y^x$ to form CAX, wherein n is an integer from about 1 to about 12, y is an integer from about 1 to about 24, and x is an integer from about 1 to about 12.

In another embodiment of this invention, a porous ceramic composition is provided that comprises a calcium aluminate (CA) containing phase, a retarder, and a surfactant, wherein said calcium aluminate containing phase results from the interaction of $C_nA_y$, $C_nA_y$-hydrates, CaO, $Al_nO_y$-hydrates with $P_nO_y^x$ to form CAX, wherein n is an integer from about 1 to about 12, y is an integer from about 1 to about 24, and x is an integer from about 1 to about 12. The porous ceramic composition optionally further comprises at least one of a fiber, water, an accelerator, a biologically active material, a source of phosphate, a reactive alumina, and combinations thereof.

In yet another embodiment of this invention, a method is provided for using a ceramic porous composition for producing artificial structures for use in-vitro or in-vivo by a patient comprising employing a porous ceramic composition comprising a calcium aluminate (CA) containing phase, a retarder, and a surfactant, as described herein, placing said porous ceramic composition into a mold wherein said mold matches a patient's pre-identified structure to form an artificial structure. The method includes wherein said calcium aluminate containing phase results from the interaction of $C_nA_y$, $C_nA_y$-hydrates, CaO, $Al_nO_y$-hydrates with $P_nO_y^x$ to form CAX, wherein n is an integer from about 1 to about 12, y is an integer from about 1 to about 24, and x is an integer from about 1 to about 12. The present ceramic porous composition may also be used as an in-situ patch for repairing a bone void of the patient that may occur, for example but not limited to, as a result of trauma and injury to the bone.

The following examples demonstrate the instant invention in greater detail. These examples are not intended to limit the scope of the invention in any way.

Example 1

|  | Wt. % |
| --- | --- |
| Calcium Aluminate (various phases) | 99 |
| Citric Acid Monohydrate | 0.2 |
| Castament FS20 | 0.55 |
| Herculon 153 fibers | 0.25 |
| Water (for casting as a 'plus' addition) | 22.0 |

In this example an inert mold of the object would be created from the three dimensional data. Common mold materials are aluminum, steel, PVC or polyurethane. Water would be added to the above mix to give it a vibration cast consistency. This mix would then be vibrated into the mold. In other examples the water addition, additives and consistency of the material could be adjusted to allow for slip casting or gel casting. The water demand of the mixture is controlled by the particle size distribution of the mix and also the surfactant (in Example 1, Castament FS20). Examples of other surfactants are, but not limited to, sodium tripolyphosphate (STP or STPP), Darvan #7, and Melflux. As will be understood by those person skilled in the art, the choice of surfactant shall affect the water demand and associated additive concentrations such that they will need to be adjusted, accordingly. In examples 1-4, water added was kept constant in order to compare other resulting properties. A typical water range can be from about 5%-75%.

The material would be allowed to 'set' (precipitation of the CA-hydrate phases). The speed of this reaction is slowed by the addition of citric acid monohydrate. Other materials that can control the reaction or 'set' time are, for example but not limited to, boric acid and anhydrous citric acid (as retarders) and lithium carbonate, sodium silicate or sodium aluminate (as accelerators).

The 'set' results in a shape exhibiting strong mechanical properties in a mechanism very similar to that of concrete. The mold would then be stripped and the shape and dried in an oven at approximately 110 degrees Celsius (C.). In this form the shape would be composed of various Calcium Aluminate phases and Calcium Aluminate hydrate phases, alumina gel, alumina (present in the CA starting material), Herculon 153 fibers (given as an example but substitution of biocompatible fiber can be accomplished). Typically this shape would now be fired at about 1000° C. During the firing process the CA-hydrates and alumina gel will be converted to the unhydrated phases (primarily CA and $CA_2$) and the alumina gel will convert to the oxide. This process will also introduce porosity in place of the chemically combined water and the organic fiber. The organic fiber is introduced to allow for interconnected porosity after burn-out. The diameter of the resulting channels is determined by controlling the diameter of the starting fiber. The presence of the fiber also gives water a pathway of escape from the shape, although this is not critical in small shapes. The resulting shape is suitable as scaffoldings or as an artificial bone structure capable of supporting stem cells that will differentiate into osteoblasts (in the case of bone). In addition, this structure can now be chemically altered to accommodate binding of proteins or other bioactive factors, promoting bone growth, for example. Once introduced in vivo, the matrix will again begin to hydrate which will allow bio-decomposition to occur while natural bone is being formed. If during the firing process, the shape is exposed to temperatures near 1550° C., $CA_6$ will be formed and re-hydration will not occur. In some cases this may be desirable, for example hip replacement, where a well defined geometric structure needs to be maintained.

A variety of other compositional examples are given here with a short explanation of possible benefits.

Example 2

|  | Wt. % |
| --- | --- |
| Calcium Aluminate (various phases) | 84 |
| Citric acid monohydrate | 0.2 |
| Reactive aluminas | 15 |
| STPP | 0.55 |
| Herculon 153 fibers | 0.25 |
| Water (for casting as a 'plus' addition) | 22.0 |

In this example reactive aluminas such as ALMATIS' A-2, A-3000 and A-1000 are added to give improved casting character and a denser, less porous final matrix. Herculon 153 fibers are fibrous materials commercially available from Hercules, Incorporated, Wilmington, Del. Darvan #7 is a sodium polymethacrylate composition used as a surfactant and is commercially available from R. T. Vanderbilt Company, Inc., Norwalk, Conn.

Example 3

|  | Wt. % |
| --- | --- |
| Calcium Aluminate (various phases) | 98.5 |
| Foaming agent | 1.0 |
| Darvan #7 | 0.5 |
| Water (for casting as a 'plus' addition) | 22.0 |

In this example a foaming agent such as CF-500 or CF-700 from Unifoam, is used to introduce a high degree of porosity to the finished material. The diameter of the porosity can be controlled by the choice of foaming agent (e.g. CF-700 gives a larger bubble) and the volume of porosity is controlled by the amount of foaming agent added.

Example 4

|  | Wt. % |
| --- | --- |
| Calcium Aluminate (various phases) | 90.5 |
| Foaming agent | 1.0 |
| Calcium orthophosphate | 8.0 |
| Melflux | 0.5 |
| Water (for casting as a 'plus' addition) | 22.0 |

In this example a phosphate source is added to give raw material for osteoblast precipitation of natural bone. Melflux is a polymeric surfactant commercially available from Degussa Construction Polymers, Kennesaw, Ga.

As can be seen in these examples there are a variety of strategies one can take in determining an appropriate starting matrix. The examples set forth herein are given to demonstrate this breadth, however, they are not intended to limit the scope of the present invention as described herein. These examples set forth herein are for the purposes of illustration and it will be evident to those persons skilled in the art that numerous variations and details of the instant invention may be made without departing from the instant invention as set forth herein.

DETAILED COMPOSITIONAL STRATEGY, EXAMPLE 5

Example 5 will be used to demonstrate a detailed compositional matrix and the resulting physical properties of the resulting solid body.

Calcium Aluminate Clinker of the following chemistry (reported on an oxide basis) was obtained for the study. The material was screened, sized and chemistry was determined on each fraction (see table I)

|  | Fraction | | | |
| --- | --- | --- | --- | --- |
| Oxide | +10 m | 10/28 m | 28/65 m | −65 m |
|  | (concentration in Wt %) | | | |
| SiO2 | 0.44 | 0.29 | 0.22 | 0.25 |
| Al2O3 | 71.59 | 71.21 | 70.35 | 71.19 |
| Fe2O3 | 0.07 | 0.01 | <0.01 | 0.01 |
| CaO | 27.38 | 28.08 | 29.02 | 27.95 |
| MgO | 0.27 | 0.22 | 0.21 | 0.31 |
| Na2O | 0.23 | 0.17 | 0.18 | 0.26 |
| K2O | 0.01 | 0.01 | 0.01 | 0.02 |
| P2O5 | 0.01 | 0.01 | 0.01 | 0.01 |

| Mineralogical Examination of these fractions showed the following: | | | | |
| --- | --- | --- | --- | --- |
| Compound | +10 m | 10/28 m | 28/65 m | −65 |
|  | Present | | | |
| CaAl2O4 (CA) | M | M | M | M |
| CaAl4O7 (CA2) | M | M | M | M |
| Ca12Al14O33 (C12A7) | m | m | t | nd |
| Ca3Al2O6 (C3A) | nd | nd | nd | nd |
| Ca5Al6O14 (C5A3) | nd | nd | nd | nd |
| Ca2Al12O5 (C2A) | nd | nd | nd | nd |
| CaAl12O19 (CA6) | nd | nd | nd | nd |
| Ca3Al10O18 (C3A5) | nd | nd | nd | nd |

-continued

Mineralogical Examination of these fractions showed the following:

| Compound | +10 m | 10/28 m | 28/65 m | −65 |
|---|---|---|---|---|
| | | Present | | |
| CaO (C) | t | t | t | t |
| Al2O3 (A) | t | t | t | t |

M = Major,
m = minor,
t = trace,
nd = not detected

This chemistry and mineralogy is typical for a 70% alumina containing CA cement. CA cements containing greater than 70% alumina can be used. CA cement containing less than 70% alumina can also be used; however, most commercially available products have impurities, which increase in concentration as the alumina content decreases. Common brands of 70% alumina containing CA cement are ALAMITIS' CA14 product and Lafarge's Secar 71 product.

The typical average open porosity of the CA aggregate is 53.5% while the TSG averages 2.9 g/cm$^3$.

Composition Example 5

| Aggregate | Wt % |
|---|---|
| CA +10 m | 15% |
| CA 10/28 m | 30% |
| CA 28/65 m | 10% |
| CA −65 m | 11% |
| CA −325 m | 7% |
| A-2 alumina | 8% |
| A-3000 alumina | 10% |
| A-1000 alumina | 9% |
| STPP (plus addition) | 0.15% |

24% by weight of water was added to give a vibration cast consistency. The material was cast into simple bars in order to determine modulus and crushing strengths. The shape was stripped from the mold in 24 hours and dried at 110° C. Finally, the shape was fired to a temperature of 1100° C. and allowed to reach thermal equilibrium. The shape was allowed to cool and was tested. The results are as follows:

Apparent porosity=50%
Average pore size=44 microns
Cold crushing strength (ASTM C133)=34.5 MPa
Modulus of Rupture (ASTM C133)=9.3 MPa Whereas particular embodiments of this invention have been described above for purposes of illustration, it will be evident to those persons skilled in the art that numerous variations of the details of the present invention may be made without departing from the invention as defined herein and in the appended claims.

What is claimed is:

1. A porous ceramic body for in vitro and in vivo use consisting essentially of a fired nonhydratable composition consisting essentially of;
a calcium aluminate (CA) containing phase that is a single nonhydratable $CA_6$ phase, and a biologically active material that comprises at least one or more proteins for promoting bone growth, and a fiber, said $CA_6$ phase, said biologically active material and said fiber forming a ceramic body having interconnected porosity and that is chemically compatible with natural bone.

2. The porous ceramic body of claim 1 having a porosity suitable for achieving vascularity.

3. The porous ceramic body of claim 1 wherein said composition is capable of being functionalized for use with biologic processes.

4. The porous ceramic body of claim 3 wherein said biological processes include accommodation of binding sites.

5. The porous ceramic body of claim 1 wherein said composition is capable of being used to repair a bone void of a patient.

6. The porous ceramic body of claim 1 that is selected from the group consisting of an artificial bone, artificial joint, in-vitro support structure, and in-vivo support structure.

7. The porous ceramic body of claim 6 wherein said in-vitro and in-vivo support structures are a scaffold matrix for support of cell, tissue, organ and nerve growth.

* * * * *